United States Patent
Yale et al.

[11] B 3,981,886
[45] Sept. 21, 1976

[54] AMINO-BENZIMIDAZOLE DERIVATIVES

[75] Inventors: Harry L. Yale, New Brunswick; James A. Bristol, Boonton, both of N.J.

[73] Assignee: E. R. Squibb & Sons, Inc., Princeton, N.J.

[22] Filed: Jan. 20, 1975

[21] Appl. No.: 542,158

[44] Published under the second Trial Voluntary Protest Program on January 13, 1976 as document No. B 542,158.

[52] U.S. Cl. ............................ 260/309.2; 424/273
[51] Int. Cl.² ........................................... C07D 235/30
[58] Field of Search ................................. 260/309.2

[56] References Cited
OTHER PUBLICATIONS

Berg et al., Chem. Abst. 1962, vol. 56, columns 11582–11584.
Reddy et al., Chem. Abst. 1970, vol. 72, No. 31695w.
Shelepin et al., Chem. Abst. 1970, vol. 73, No. 76345u.
Yutilov et al., Chem. Abst. 1965, vol. 63, column 16335.

Primary Examiner—Natalie Trousof
Attorney, Agent, or Firm—Lawrence S. Levinson; Merle J. Smith; Burton Rodney

[57] ABSTRACT

Amino-benzimidazole derivatives of the structure

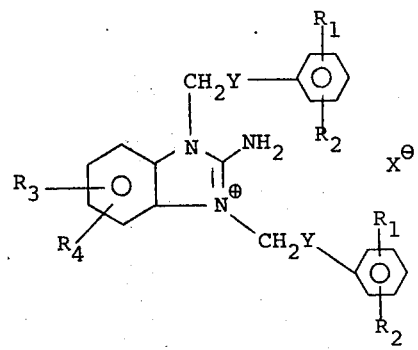

are provided which are useful as anti-inflammatory agents. In addition, a method for preparing such compounds, pharmaceutical compositions containing such compounds, and methods for using such pharmaceutical compositions in the treatment of inflammation are taught.

12 Claims, No Drawings

AMINO-BENZIMIDAZOLE DERIVATIVES

This invention relates to compounds of the formula:

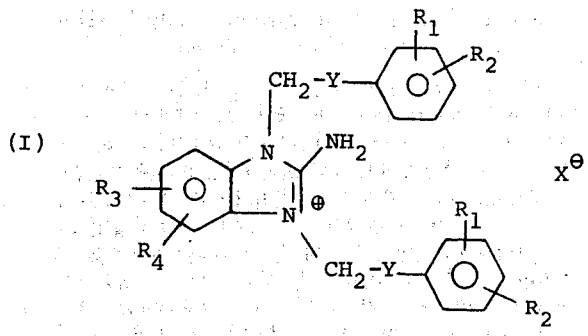

(I)

wherein
- Y is oxygen or sulfur;
- $R_1$ and $R_2$ are the same or different and may be hydrogen, halo, lower alkyl, lower alkoxy, trifluoromethyl, or N,N-dimethylsulfonamido;
- $R_3$ and $R_4$ are the same or different and may be hydrogen, lower alkyl, lower alkoxy, aryl, halo, aralkyl, or substituted aryl; and
- X is Cl, Br or I.

The preferred compounds of this invention are those wherein Y is oxygen, $R_3$ and $R_4$ are hydrogen, or one of $R_3$ and $R_4$ is halogen and the other is hydrogen, $R_1$ is halo, and $R_2$ is hydrogen or halo, and the most preferred being those wherein Y is oxygen, $R_3$ and $R_4$ are hydrogen, $R_1$ is chloro, $R_2$ is hydrogen or chloro and X is chlorine.

Other compounds of this invention are those of formula I wherein $R_1$ and $R_2$ are hydrogen, halo, lower alkyl, lower alkoxy or trifluoromethyl; hydrogen, halo, lower alkyl or lower alkoxy; hydrogen, halo, lower alkyl or N,N-dimethylsulfonamido; hydrogen, halo or lower alkyl; hydrogen, halo or trifluoromethyl; and wherein $R_3$ and $R_4$ are hydrogen, lower alkyl, lower alkoxy, phenyl or naphthyl; hydrogen, lower alkyl, phenyl, naphthyl, phenyl lower alkyl, naphthyl lower alkyl, phenyl including an $R_1$ or $R_2$ substituent, or naphthyl including an $R_1$ or $R_2$ substituent; or hydrogen, lower alkyl or halo.

The lower alkyl groups represented by the above $R_1$, $R_2$, $R_3$ and $R_4$ groups include straight or branched chain aliphatic hydrocarbon radicals having up to seven carbon atoms, such as methyl, ethyl, propyl, isopropyl, butyl, isobutyl, t-butyl, amyl, hexyl, heptyl and the like.

The alkoxy group includes straight and branched chain radicals of up to and including seven carbons atoms, corresponding to the above alkyl groups, e.g., methoxy, ethoxy, propoxy, isopropoxy and the like.

The term "halo" includes each of the four halogens but bromine and chlorine are preferred.

The term "aryl" includes monocyclic or bicyclic monovalent aromatic ring systems such as phenyl or naphthyl. These aryl radicals can include as substituents any of the $R_1$ or $R_2$ groups mentioned hereinbefore.

The term "aralkyl" encompasses a lower alkyl group as defined above substituted with an aryl group as defined above, such as benzyl or phenethyl.

In addition, in accordance with the present invention, a method is provided for preparing compounds of the present invention (I) by reacting a 2-aminobenzimidazole of the structure (II) 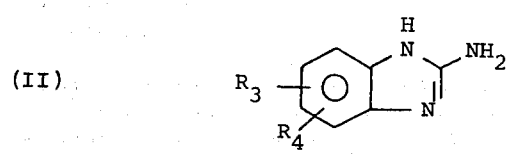

wherein $R_3$ and $R_4$ are as defined above, with a phenyloxy (or thio) methyl halide of the formula (III) 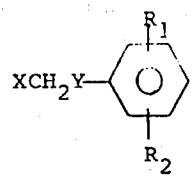

wherein X, Y, $R_1$ and $R_2$ are as defined above.

The above reaction is carried out under anhydrous conditions in the presence of one or more of a variety of solvents such as sulfolane (tetramethylsulfone), or aromatic solvents such as toluene, xylene, diethylbenzene, cumene, or trimethylbenzene, with sulfolane being preferred. In addition, it is preferred that each of the compounds (II) and (III) be separately dissolved in the same solvent before they are admixed with one another.

The temperatures and reaction times employed in carrying out the above reaction may range from 0° to 150°C for periods of about 1 hour to 10 days, and preferably from about 20° to about 40°C for 1 to 10 days where sulfolane is employed as the solvent, and from about 80° to about 150°C for 1 to 24 hours where an aromatic solvent is employed.

The molar ratio of the 2-aminobenzimidazole (II) to the phenyloxy (or thio) methyl halide (III) can range from about 1:8 to about 1:1 and preferably from about 1:3 to about 1:1, and optimally 1:2 or 1:1.

The preparation of a variety of 2-aminobenzimidazoles which may be employed as starting materials herein is well documented in Weissberger's "The Chemistry of Heterocyclic Compounds, Imidazole and Its Derivatives", Interscience Publishers Co., New York, 1953.

It will be understood that unsubstituted 2-aminobenzimidazoles (II), that is where $R_3$ and $R_4$ are hydrogen, can be employed to form compounds of Formula (I), and thereafter other $R_3$ and/or $R_4$ radicals may be inserted in the 2-aminobenzimidazole ring in place of one or two hydrogens, employing conventional procedures as will be apparent to one skilled in the art.

The phenyloxy (or thio) methyl halide (III) can be prepared as described in the paper entitled "Novel Polycyclic Heterocycles. XI" by R. B. Petigara et al., Journal of Heterocyclic Chemistry, 11, 331 (1974) as well as in copending applications Ser. No. 382,803, filed July 26, 1973, and Ser. No. 525,143, filed Nov. 19, 1974.

The compounds of this invention have been found to be useful as antiinflammatory agents in mammals, such as rats, mice, dogs and the like, when administered in amounts ranging from about 1.2 mg. to about 30 mg. per kg. of body weight per day. A preferred dosage regimen for optimum results would be from about 1.5 mg. to about 15 mg. per kg. of body weight per day, and such dosage units are employed that a total of from about 100 mg. to about 2 g. of active ingredient for a subject of about 70 kg. body weight is administered in a 24 hour period.

The compounds of the present invention in the described dosages are intended to be administered orally; however, other routes such as rectally, intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5 to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 200 milligrams of active compound.

The tablets, troches, pills, capsules and the like may also contain the following: a binder such as gum tragacanth, acacia, corn starch or gelatin; and excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The invention will be described in greater detail in conjunction with the following specific examples.

The following examples are provided for illustrative purposes and may include particular features of the invention; however, the examples should not be construed as limiting the invention, many variations of which are possible without departing from the spirit or scope thereof. All temperatures are on the Centigrade scale.

EXAMPLE 1

2-Amino-1,3-bis[(2-bromophenoxy)methyl]-1H-benzimidazol-3-ium chloride o-Bromo-α-chloroanisole 15.0 g (0.0679 mol) in 20 ml of sulfolane is added to a solution of 4.50 g (0.0339 mol) of 2-aminobenzimidazole in 40 ml of sulfolane. The mixture turns into a semi-solid mass upon standing for several hours. After standing for 6.75 days at room temperature, the reaction mixture is diluted with 40 ml of 2-propanol, filtered, and the product is washed with 2-propanol. Trituration with ether gives 7.7 g (43%) of a white solid; mp 229°–230°. Recrystallization of 3.5 g of this material from 340 ml of 90% ethanol gives 2.5 g of the named product as a white fluffy solid after drying for 6 hours at 78° (1 mm): mp 236°–237°dec.

Anal. Calcd for $C_{21}H_{18}Br_2N_3O_2.Cl$: C, 46.79; H, 3.39; N, 7.80; Cl, 6.58. Found: C, 46.82; H, 3.66; N, 7.79; Cl, 6.76.

EXAMPLE 2

2-Amino-1,3-bis[(2-bromo-4-chlorophenoxy)methyl]-1H-benzimidazol-3-ium chloride

A mixture of 1.00 g (0.00745 mol) of 2-aminobenzimidazole and 1.91 g (0.00745 mol) of 2-bromo-4-chlorophenyl chloromethyl ether in 5 ml of sulfolane is allowed to stand at room temperature for 22 hours. A solid precipitate forms within 5 minutes of mixing the two reagents. The product mixture is diluted with 10 ml of cold 2-propanol, and filtered, and the solid product is washed with two portions of cold 2-propanol. Drying in vacuo over $P_2O_5$ gives 2.28 g (100% crude yield) of the product as a white solid: mp 230° sinters, melts 233°–234° dec. The product is dissolved in 400 ml of hot 95% ethanol, and the solution is concentrated to a volume of 200 ml. The solution is allowed to cool slowly while precipitating a white floculant solid which is isolated from the chilled mixture to give 1.11 g (49% yield) of the named product: mp 235°–236°dec.

Anal. Calcd for $C_{21}H_{16}Br_2Cl_3N_3O_2$: C, 41.48; H, 2.65; N, 6.91; Cl, 17.47. Found: C, 41.75; H, 2.93; N, 6.99; Cl, 17.70.

EXAMPLE 3

2-Amino-1,3-bis[(3-chlorophenoxy)methyl]-1H-benzimidazol-3-ium chloride

Following the procedure of Example 2 and replacing 2-bromo-4-chlorophenyl chloromethyl ether with 3-chlorophenyl chloromethyl ether, the title compound is obtained.

EXAMPLE 4

2-Amino-1,3-bis[(4-methylphenoxy)methyl]-1H-benzimidazol-3-ium bromide

Following the procedure of Example 2 and replacing 2-bromo-4-chlorophenyl chloromethyl ether with 4- methylphenyl bromomethyl ether, the title compound is obtained.

EXAMPLE 5

2-Amino-1,3-bis[(2-ethoxyphenoxy)methyl]-1H-benzimidazol-3-ium iodide

Following the procedure of Example 2 and replacing 2-bromo-4-chlorophenyl chloromethyl ether with 2-ethoxyphenyl iodomethyl ether, the title compound is obtained.

EXAMPLE 6

2-Amino-1,3-bis[(3-trifluoromethylphenoxy)methyl]-1H-benzimidazol-3-ium chloride Following the procedure of Example 2 and replacing 2-bromo-4-chlorophenyl chloromethyl ether with 3-trifluoromethylphenyl chloromethyl ether, the title compound is obtained.

EXAMPLE 7

2-Amino-1,3-bis[(4-N,N-dimethylsulfonamidophenoxy)methyl]-1H-benzimidazol-3-ium chloride Following the procedure of Example 2 and replacing 2-bromo-4-chlorophenyl chloromethyl ether with 4-N,N-dimethylsulfonamidophenyl chloromethyl ether, the title compound is obtained.

EXAMPLE 8

2-Amino-1,3-bis[(2-bromo-4-methylphenoxy)methyl]-1H-benzimidazol-3-ium bromide

Following the procedure of Example 2 and replacing 2-bromo-4-chlorophenyl chloromethyl ether with 2-bromo-4-methylphenyl bromomethyl ether, the title compound is obtained.

EXAMPLE 9

2-Amino-1,3-bis[(3-fluoro-4-t-butylphenoxy)methyl]-1H-benzimidazol-3-ium chloride Following the procedure of Example 2 and replacing 2-bromo-4-chlorophenyl chloromethyl ether with 3-fluoro-4-t-butylphenyl chloromethyl ether, the title compound is obtained.

EXAMPLE 10

2-Amino-1,3-bis[(4-chloro-3-n-propoxyphenoxy)methyl]-1H-benzimidazol-3-ium chloride Following the procedure of Example 2 and replacing 2-bromo-4-chlorophenyl chloromethyl ether with 4-chloro-3-n-propoxyphenyl chloromethyl ether, the title compound is obtained.

EXAMPLE 11

2-Amino-1,3-bis[(2-ethyl-5-methoxyphenoxy)methyl]-1H-benzimidazol-3-ium bromide

Following the procedure of Example 2 and replacing 2-bromo-4-chlorophenyl chloromethyl ether with 2-ethyl-5-methoxyphenyl chloromethyl ether, the title compound is obtained.

EXAMPLE 12

2-Amino-1,3bis[(2-bromo-4-trifluoromethylphenoxy)methyl]-1H-benzimidazol-3-ium chloride Following the procedure of Example 2 and replacing 2-bromo-4-chlorophenyl chloromethyl ether with 2-bromo-4-trifluoromethylphenyl chloromethyl ether, the title compound is obtained.

EXAMPLE 13

2-Amino-1,3-bis[(3-chloro-4-N,N-dimethylsulfonamidophenoxy)methyl]-1H-benzimidazol-3-ium iodide Following the procedure of Example 2 and replacing 2-bromo-4-chlorophenyl chloromethyl ether with 3-chloro-4-N,N-dimethylsulfonamidophenyl iodomethyl ether, the title compound is obtained.

EXAMPLE 14

2-Amino-1,3-bis[(6-ethyl-2-trifluoromethylphenoxy)methyl]-1H-benzimidazol-3-ium bromide Following the procedure of Example 2 and replacing 2-bromo-4-chlorophenyl chloromethyl ether with 6-ethyl-2-trifluoromethylphenyl bromomethyl ether, the title compound is obtained.

EXAMPLE 15

2-Amino-1,3-bis[(4-N,N-dimethylsulfonamido-3-ethylphenoxy)methyl]-1H-benzimidazol-3-ium chloride Following the procedure of Example 2 and replacing 2-bromo-4-chlorophenyl chloromethyl ether with 4-N,N-dimethylsulfonamido-3-ethylphenyl chloromethyl ether, the title compound is obtained.

EXAMPLE 16

2-Amino-1,3-bis[(2-ethoxy-6-trifluoromethylphenoxy)methyl]-1H-benzimidazol-3-ium bromide Following the procedure of Example 2 and replacing 2-bromo-4-chlorophenyl chloromethyl ether with 2-ethoxy-6-trifluoromethylphenyl bromomethyl ether, the title compound is obtained.

EXAMPLE 17

2-Amino-1,3-bis[(2-s-butoxy-4-N,N-dimethyl sulfonamidophenoxy)methyl]-1H-benzimidazol-3-ium iodide Following the procedure of Example 2 and replacing 2-bromo-4-chlorophenyl chloromethyl ether with 2-s-butoxy-4-N,N-dimethylsulfonamidophenyl iodomethyl ether, the title compound is obtained.

EXAMPLE 18

2-Amino-1,3-bis[(4-N,N-dimethylsulfonamido-2-trifluoromethylphenoxy)methyl]-1H-benzimidazol-3-ium chloride Following the procedure of Example 2 and replacing 2-bromo-4-chlorophenyl chloromethyl ether with 4-N,N-dimethylsulfonamidophenyl chloromethyl ether, the title compound is obtained.

EXAMPLE 19

2-Amino-1,3-bis[(2-bromophenylthio)methyl]-1H-benzimidazol-3-ium chloride

Following the procedure of Example 2 and replacing 2-bromo-4-chlorophenyl chloromethyl ether with 2-bromophenyl chloromethyl sulfide, the title compound is obtained.

EXAMPLE 20

2-Amino-1,3-bis[(2-bromo-5-chlorophenylthio)methyl]-1H-benzimidazol-3-ium chloride Following the procedure of Example 2 and replacing 2-bromo-4-chlorophenyl chloromethyl ether with 2-bromo-5-chlorophenyl chloromethyl sulfide, the title compound is obtained.

EXAMPLE 21

2-Amino-1,3-bis[(3-chlorophenylthio)methyl]-1H-benzimidazol-3-ium chloride

Following the procedure of Example 2 and replacing 2-bromo-4-chlorophenyl chloromethyl ether with 3-chlorophenyl chloromethyl sulfide, the title compound is obtained.

EXAMPLE 22

2-Amino-1,3-bis[(4-methylphenylthio)methyl]-1H-benzimidazol-3-ium bromide

Following the procedure of Example 2 and replacing 2-bromo-4-chlorophenyl chloromethyl ether with 4-methylphenyl bromomethyl sulfide, the title compound is obtained.

EXAMPLE 23

2-Amino-1,3-bis[(2-ethoxyphenylthio)methyl]-1H-benzimidazol-3-ium iodide

Following the procedure of Example 2 and replacing 2-bromo-4-chlorophenyl chloromethyl ether with 2-ethoxyphenyl iodomethyl sulfide, the title compound is obtained.

EXAMPLE 24

2-Amino-1,3-bis[(3-trifluoromethylphenylthio)methyl]-1H-benzimidazol-3-ium chloride Following the procedure of Example 2 and replacing 2-bromo-4-chlorophenyl chloromethyl ether with 3-trifluoromethylphenyl chloromethyl sulfide, the title compound is obtained.

EXAMPLE 25

2-Amino-1,3bis[(4-N,N-dimethylsulfonamidophenylthio)methyl]-1H-benzimidazol-3-ium chloride Following the procedure of Example 2 and replacing 2-bromo-4-chlorophenyl chloromethyl ether with 4-N,N-dimethylsulfonamidophenyl chloromethyl sulfide, the title compound is obtained.

EXAMPLE 26

2-Amino-1,3-bis[(2-bromo-4-methylphenylthio)methyl]-1H-benzimidazol-3-ium bromide Following the procedure of Example 2 and replacing 2-bromo-4-chlorophenyl chloromethyl ether with 2-bromo-4-methylphenyl bromomethyl sulfide, the title compound is obtained.

EXAMPLE 27

2-Amino-1,3-bis[(3-fluoro-4-t-butylphenylthio)methyl]-1H-benzimidazol-3-ium chloride Following the procedure of Example 2 and replacing 2-bromo-4-chlorophenyl chloromethyl ether with 3-fluoro-4-t-butylphenyl chloromethyl sulfide, the title compound is obtained.

EXAMPLE 28

2-Amino-1,3-bis[(4-chloro-3-n-propoxyphenylthio)methyl]-1H-benzimidazol-3-ium chloride Following the procedure of Example 2 and replacing 2-bromo-4-chlorophenyl chloromethyl ether with 4-chloro-3-n-propoxyphenyl chloromethyl sulfide, the title compound is obtained.

EXAMPLE 29

2-Amino-1,3-bis[(2-ethyl-5-methoxyphenylthio)methyl]-1H-benzimidazol-3-ium bromide Following the procedure of Example 2 and replacing 2-bromo-4-chlorophenyl chloromethyl ether with 2-ethyl-5-methoxyphenyl chloromethyl sulfide, the title compound is obtained.

EXAMPLE 30

2-Amino-1,3-bis[(2-bromo-4-trifluoromethylphenylthio)methyl]-1H-benzimidazol-3-ium chloride Following the procedure of Example 2 and replacing 2-bromo-4-chlorophenyl chloromethyl ether with 2-bromo-4-trifluoromethylphenyl chloromethyl sulfide, the title compound is obtained.

EXAMPLE 31

2-Amino-1,3-bis[(3-chloro-4-N,N-dimethylsulfonamidophenylthio)methyl]-1H-benzimidazol-3-ium iodide Following the procedure of Example 2 and replacing 2-bromo-4-chlorophenyl chloromethyl ether with 3-chloro-4-N,N-dimethylsulfonamidophenyl iodomethyl sulfide, the title compound is obtained.

EXAMPLE 32

2-Amino-1,3-bis[(6-ethyl-2-trifluoromethylphenylthio)methyl]-1H-benzimidazol-3-ium bromide Following the procedure of Example 2 and replacing 2-bromo-4-chlorophenyl chloromethyl ether with 6-ethyl-2-trifluoromethylphenyl bromomethyl sulfide, the title compound is obtained.

EXAMPLE 33

2-Amino-1,3-bis[(4-N,N-dimethylsulfonamido-3-ethylphenylthio)methyl]-1H-benzimidazol-3-ium chloride Following the procedure of Example 2 and replacing 2-bromo-4-chlorophenyl chloromethyl ether with 4-N,N-dimethylsulfonamido-3-ethylphenyl chloromethyl sulfide, the title compound is obtained.

EXAMPLE 34

2-Amino-1,3-bis[(2-ethoxy-6-trifluoromethylphenylthio)methyl]-1H-benzimidazol-3-ium bromide Following the procedure of Example 2 and replacing 2-bromo-4-chlorophenyl chloromethyl ether with 2-ethoxy-6-trifluoromethylphenyl bromomethyl sulfide, the title compound is obtained.

EXAMPLE 35

2-Amino-1,3-bis[(2-s-butoxy-4-N,N-dimethyl sulfonamidophenylthio))methyl]-1H-benzimidazol-3-ium iodide Following the procedure of Example 2 and replacing 2-bromo-4-chlorophenyl chloromethyl ether with 2-s-butoxy-4-N,N-dimethylsulfonamidophenyl iodomethyl sulfide, the title compound is obtained.

EXAMPLE 36

2-Amino-1,3-bis[(4-N,N-dimethylsulfonamido-2-trifluoromethylphenylthio)methyl]-1H-benzimidazol-3-ium chloride Following the procedure of Example 2 and replacing 2-bromo-4-chlorophenyl chloromethyl ether with 4-N,N-dimethylsulfonamidophenyl chloromethyl sulfide, the title compound is obtained.

EXAMPLE 37

2-Amino-4-methyl-1,3-bis[(3-chlorophenoxy)methyl]-1H-benzimidazol-3-ium chloride Following the procedure of Example 2 and replacing 2-aminobenzimidazole with 2-amino-4-methylbenzimidazole and replacing 2-bromo-4-chlorophenyl chloromethyl ether with 3-chlorophenyl chloromethyl ether, the title compound is obtained.

EXAMPLE 38

2-Amino-5-ethoxy-1,3-bis[(2-bromophenoxy)methyl]-1H-benzimidazol-3-ium chloride

Following the procedure of Example 2 and replacing 2-aminobenzimidazole with 2-amino-5-ethoxybenzimidazole and replacing 2-bromo-4-chlorophenyl chloromethyl ether with 2-bromophenyl chloromethyl ether, the title compound is obtained.

EXAMPLE 39

2-Amino-6-phenyl-1,3-bis[(2,4-dichlorophenxoy)methyl]-1H-benzimidazol-3-ium bromide Following the procedure of Example 2 and replacing 2-aminobenzimidazole with 2-amino-6-phenylbenzimidazole and replacing 2-bromo-4-chlorophenyl chloromethyl ether with 2,4-dichlorophenyl bromomethyl ether, the title compound is obtained.

EXAMPLE 40

2-Amino-7-chloro-1,3-bis[(3-methylphenoxy)methyl]-1H-benzimidazol-3-ium chloride Following the procedure of Example 2 and replacing 2-aminobenzimidazole with 2-amino-7-chlorobenzimidazole and replacing 2-bromo-4-chlorophenyl chloromethyl ether with 3-methylphenyl chloromethyl ether, the title compound is obtained.

EXAMPLE 41

2-Amino-5-benzyl-1,3-bis[(3,5-diethylphenoxy)methyl]-1H-benzimidazol-3-ium iodide Following the procedure of Example 2 and replacing 2-aminobenzimidazole with 2-amino-5-benzylbenzimidazole and replacing 2-bromo-4-chlorophenyl chloromethyl ether with 3,5-diethylphenyl iodomethyl ether, the title compound is obtained.

EXAMPLE 42

2-Amino-5-(2-bromophenyl)-1,3-bis[(2-trifluoromethylphenoxy)methyl]-1H-benzimidazol-3-ium chloride Following the procedure of Example 2 and replacing 2-aminobenzimidazole with 2-amino-5-(2-bromophenyl)benzimidazole and replacing 2-bromo-4-chlorophenyl chloromethyl ether with 2-trifluoromethylphenyl chloromethyl ether, the title compound is obtained.

EXAMPLE 43

2-Amino-5-(2,6-dichlorophenyl)-1,3-bis[(4-N,N-dimethylsulfonamidophenoxy)methyl]-1H-benzimidazol-3-ium chloride Following the procedure of Example 2 and replacing 2-aminobenzimidazole with 2-amino-5-(2,6-dichlorophenyl)benzimidazole and replacing 2-bromo-4-chlorophenyl chloromethyl ether with 4-N,N-dimethylsulfonamidophenyl chloromethyl ether, the title compound is obtained.

EXAMPLE 44

2-Amino-4-(2-ethyl-3-methoxyphenyl)-1,3-bis[(3-methyl-4-propylphenoxy)methyl]-1H-benzimidazol-3-ium bromide Following the procedure of Example 2 and replacing 2-aminobenzimidazole with 2-amino-4-(2-ethyl-3-methoxyphenyl)benzimidazole and replacing 2-bromo-4-chlorophenyl chloromethyl ether with 3-methyl-4-propylphenyl bromomethyl ether, the title compound is obtained.

EXAMPLE 45

2-Amino-7-(3-t-butyl-5-trifluoromethylphenyl)-1,3-bis[(2-bromo-4-N,N-dimethylsulfonamidophenoxy)methyl]-1H-benzimidazol-3-ium iodide Following the procedure of Example 2 and replacing 2-aminobenzimidazole with 2-amino-7-(3-t-butyl-5-trifluoromethylphenyl)benzimidazole and replacing 2-bromo-4-chlorophenyl chloromethyl ether with 2-bromo-4-N,N-dimethylsulfonylamidophenyl iodomethyl ether, the title compound is obtained.

EXAMPLE 46

2-Amino-5,6-dichloro-1,3-bis[(2-bromophenoxy)methyl]-1H-benzimidazol-3-ium chloride Following the procedure of Example 2 and replacing 2-aminobenzimidazole with 2-amino-5,6-dichlorobenzimidazole and replacing 2-bromo-4-chlorophenyl chloromethyl ether with 2-bromophenyl chloromethyl ether, the title compound is obtained.

EXAMPLE 47

2-Amino-5,6-dimethoxy-1,3-bis[(2-chloro-3-iodophenoxy)methyl]-1H-benzimidazol-3-ium chloride Following the procedure of Example 2 and replacing 2-aminobenzimidazole with 2-amino-5,6-dimethoxybenzimidazole and replacing 2-bromo-4-chlorophenyl chloromethyl ether with 2-chloro-3-iodophenyl chloromethyl ether, the title compound is obtained.

EXAMPLE 48

2-Amino-5,6-dimethyl-1,3-bis[(3,5-dibromophenoxy)-methyl]-1H-benzimidazol-3-ium chloride Following the procedure of Example 2 and replacing 2-aminobenzimidazole with 2-amino-5,6-dimethylbenzimidazole and replacing 2-bromo-4-chlorophenyl chloromethyl ether with 3,5-dibromophenyl chloromethyl ether, the title compound is obtained.

EXAMPLE 49

2-Amino-5,7-bis-trifluoromethyl-1,3-bis[(2-bromo-4-fluorophenoxy)methyl]-1H-benzimidazol-3-ium chloride Following the procedure of Example 2 and replacing 2-aminobenzimidazole with 2-amino-5,7-bis-trifluoromethylbenzimidazole and replacing 2-bromo-4-chlorophenyl chloromethyl ether with 2-bromo-4-fluorophenyl chloromethyl ether, the title compound is obtained.

EXAMPLE 50

2-Amino-5-ethoxy-1,3-bis[(2-bromophenylthio)methyl]-1H-benzimidazol-3-ium chloride Following the procedure of Example 2 and replacing 2-aminobenzimidazole with 2-amino-5-ethoxybenzimidazole and replacing 2-bromo-4-chlorophenyl chloromethyl ether with 2-bromophenyl chloromethyl sulfide, the title compound is obtained.

EXAMPLE 51

2-Amino-6-phenyl-1,3-bis[(2,4-dichlorophenylthio)-methyl]-1H-benzimidazol-3-ium bromide Following the procedure of Example 2 and replacing 2-aminobenzimidazole with 2-amino-6-phenylbenzimidazole and replacing 2-bromo-4-chlorophenyl chloromethyl ether with 2,4-dichlorophenyl bromomethyl sulfide, the title compound is obtained.

EXAMPLE 52

2-Amino-7-chloro-1,3-bis[(3-methylphenylthio)methyl]-1H-benzimidazol-3-ium chloride Following the procedure of Example 2 and replacing 2-aminobenzimidazole with 2-amino-7-chlorobenzimidazole and replacing 2-bromo-4-chlorophenyl chloromethyl ether with 3-methylphenyl chloromethyl sulfide, the title compound is obtained.

EXAMPLE 53

2-Amino-5-benzyl-1,3-bis[(3,5-diethylphenylthio)methyl]-1H-benzimidazol-3-ium iodide Following the procedure of Example 2 and replacing 2-aminobenzimidazole with 2-amino-5-benzylbenzimidazole and replacing 2-bromo-4-chlorophenyl chloromethyl ether with 3,5-diethylphenyl iodomethyl sulfide, the title compound is obtained.

EXAMPLE 54

2-Amino-5-(2-bromophenyl)-1,3-bis[(2-trifluoromethylphenylthio)methyl]-1H-benzimidazol-3-ium chloride Following the procedure of Example 2 and replacing 2-aminobenzimidazole with 2-amino-5-(2-bromophenyl)benzimidazole and replacing 2-bromo-4-chlorophenyl chloromethyl ether with 2-trifluoromethylphenyl chloromethyl sulfide, the title compound is obtained.

EXAMPLE 55

2-Amino-5-(2,6-dichlorophenyl)-1,3-bis[(4-N,N-dimethylsulfonamidophenylthio)methyl]-1H-benzimidazol-3-ium chloride Following the procedure of Example 2 and replacing 2-aminobenzimidazole with 2-amino-5-(2,6-dichlorophenyl)benzimidazole and replacing 2-bromo-4-chlorophenyl chloromethyl ether with 4-N,N-dimethylsulfonamidophenyl chloromethyl sulfide, the title compound is obtained.

EXAMPLE 56

2-Amino-4-(2-ethyl-3-methoxyphenyl)-1,3-bis[(3-methyl-4-propylphenylthio)methyl]-1H-benzimidazol-3-ium bromide Following the procedure of Example 2 and replacing 2-aminobenzimidazole with 2-amino-4-(2-ethyl-3-methoxyphenyl)benzimidazole and replacing 2-bromo-4-chlorophenyl chloromethyl ether with 3-methyl-4-propylphenyl bromomethyl sulfide, the title compound is obtained.

EXAMPLE 57

2-Amino-7-(3-t-butyl-5-trifluoromethylphenyl)-1,3-bis[(2-bromo-4-N,N-dimethylsulfonamidophenylthio)-methyl]-1H-benzimidazol-3-ium iodide Following the procedure of Example 2 and replacing 2-aminobenzimidazole with 2-amino-7-(3-t-butyl-5-trifluoromethylphenyl)benzimidazole and replacing 2-bromo-4-chlorophenyl chloromethyl ether with 2-bromo-4-N,N-dimethylsulfonylamidophenyl iodomethyl sulfide, the title compound is obtained.

EXAMPLE 58

2-Amino-5,6-dichloro-1,3-bis[(2-bromophenylthio)-methyl]-1H-benzimidazol-3-ium chloride Following the procedure of Example 2 and replacing 2-aminobenzimidazole with 2-amino-5,6-dichlorobenzimidazole and replacing 2-bromo-4-chlorophenyl chloromethyl ether with 2-bromophenyl chloromethyl sulfide, the title compound is obtained.

EXAMPLE 59

2-Amino-5,6-dimethoxy-1,3-bis[(2-chloro-3-iodo-phenylthio)methyl]-1H-benzimidazol-3-ium chloride Following the procedure of Example 2 and replacing 2-aminobenzimidazole with 2-amino-5,6-dimethoxybenzimidazole and replacing 2-bromo-4-chlorophenyl chloromethyl ether with 2-chloro-3-iodophenyl chloromethyl sulfide, the title compound is obtained.

EXAMPLE 60

2-Amino-5,6-dimethyl-1,3-bis[(3,5-dibromophenylthio)methyl]-1H-benzimidazol-3-ium chloride Following the procedure of Example 2 and replacing 2-aminobenzimidazole with 2-amino-5,6-dimethylbenzimidazole and replacing 2-bromo-4-chlorophenyl chloromethyl ether with 3,5-dibromophenyl chloromethyl sulfide, the title compound is obtained.

EXAMPLE 61

2-Amino-5,7-bis-trifluoromethyl-1,3-bis[(2-bromo-4-fluorophenylthio)methyl]-1H-benzimidazol-3-ium chloride Following the procedure of Example 2 and replacing 2-aminobenzimidazole with 2-amino-5,7-bis-trifluoromethylbenzimidazole and replacing 2-bromo-4-chlorophenyl chloromethyl ether with 2-bromo-4-fluorophenyl chloromethyl sulfide, the title compound is obtained.

EXAMPLE 62

Preparation of Oral Syrup Formulation

| Ingredient | Amount |
|---|---|
| 2-Amino-1,3-bis[(2-bromophenoxy)methyl]-1H-benzimidazol-3-ium chloride | 1000 mg. |
| Sorbitol solution (70% N.F.) | 40 ml. |
| Sodium benzoate | 150 mg. |
| Saccharin | 15 mg. |
| Red dye (F.D. & C. No. 2) | 10 mg. |
| Cherry flavor | 50 mg. |
| Distilled water, q.s. ad | 100 ml. |

The sorbitol solution is added to 40 ml. of distilled water and the active ingredient is suspended therein. The saccharin, sodium benzoate, flavor and dye are added and dissolved in the above solution. The volume is adjusted to 100 ml. with distilled water.

Other ingredients may replace those listed in the above formulation. For example, a suspending agent such as bentonite magma, tragacanth, carboxymethylcellulose or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the structure

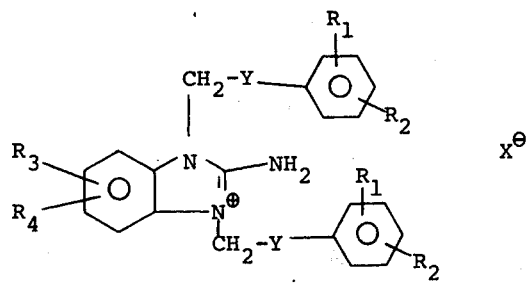

wherein
Y is oxygen or sulfur;
$R_1$ and $R_2$ are the same or different and are selected from the group consisting of hydrogen, halo, lower alkyl, lower alkoxy, trifluoromethyl or N,N-dimethylsulfonamido;
$R_3$ and $R_4$ are the same or different and are selected from the group consisting of hydrogen, lower alkyl, lower alkoxy, halo, phenyl, naphthyl, phenyl lower alkyl, naphthyl lower alkyl, or phenyl or naphthyl substituted with an $R_1$ or $R_2$ group; and
X is selected from the group consisting of Cl, Br or I.

2. A compound of claim 1 wherein $R_1$ and $R_2$ are selected from the group consisting of hydrogen, halo, lower alkyl, lower alkoxy and trifluoromethyl.

3. A compound of claim 1 wherein $R_1$ and $R_2$ are selected from the group consisting of hydrogen, halo, lower alkyl and lower alkoxy.

4. A compound of claim 1 wherein $R_1$ and $R_2$ are selected from the group consisting of hydrogen, halo, lower alkyl and N,N-dimethylsulfonamido.

5. A compound of claim 1 wherein $R_1$ and $R_2$ are selected from the group consisting of hydrogen, halo, and lower alkyl.

6. A compound of claim 1 wherein $R_1$ and $R_2$ are selected from the group consisting of hydrogen, halo and trifluoromethyl.

7. A compound of claim 1 wherein $R_3$ and $R_4$ are selected from the group consisting of hydrogen, lower alkyl, lower alkoxy, phenyl, naphthyl, and halo.

8. A compound of claim 1 wherein $R_3$ and $R_4$ are selected from the group consisting of hydrogen, lower alkyl, phenyl, naphthyl, phenyl lower alkyl, naphthyl lower alkyl, phenyl including an $R_1$ or $R_2$ substituent or naphthyl including an $R_1$ or $R_2$ substituent.

9. A compound of claim 1 wherein $R_3$ and $R_4$ are selected from the group consisting of hydrogen, lower alkyl and halo.

10. A compound of claim 1 wherein Y is oxygen, $R_3$ and $R_4$ are hydrogen, and $R_1$ is halo, $R_2$ is hydrogen or halo.

11. A compound of claim 1 having the structure

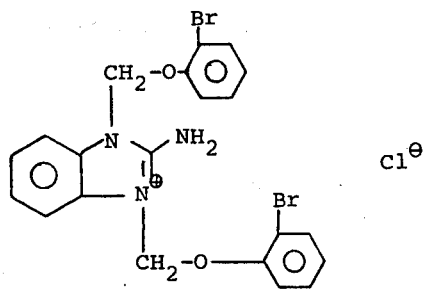

12. A compound of claim 1 having the structure

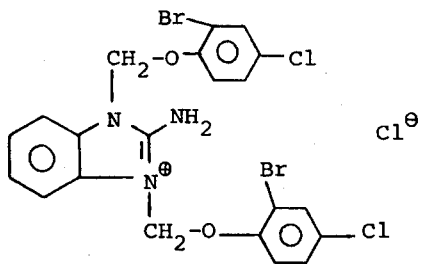

* * * * *